(12) United States Patent
Kwan

(10) Patent No.: US 8,916,090 B2
(45) Date of Patent: Dec. 23, 2014

(54) ENDOSCOPIC CAMERA COMPONENT MANUFACTURING METHOD

(75) Inventor: Kin Ming Kwan, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 346 days.

(21) Appl. No.: 13/178,321

(22) Filed: Jul. 7, 2011

(65) Prior Publication Data

US 2013/0012773 A1    Jan. 10, 2013

(51) Int. Cl.
| | |
|---|---|
| B22F 3/12 | (2006.01) |
| B22F 3/24 | (2006.01) |
| B22F 5/10 | (2006.01) |
| A61B 1/005 | (2006.01) |
| B23P 13/00 | (2006.01) |
| A61B 1/00 | (2006.01) |
| G02B 23/24 | (2006.01) |
| G02B 7/10 | (2006.01) |

(52) U.S. Cl.
CPC ............... B22F 3/24 (2013.01); A61B 1/0011 (2013.01); G02B 7/10 (2013.01); B22F 5/10 (2013.01); G02B 23/2476 (2013.01); A61B 1/00188 (2013.01)
USPC ............... 419/28; 419/36; 600/109; 359/808; 359/809; 359/811; 359/819

(58) Field of Classification Search
USPC ............... 419/28, 36; 600/109; 359/808, 809, 359/811, 819
See application file for complete search history.

(56) References Cited

U.S. PATENT DOCUMENTS

| | | | |
|---|---|---|---|
| 4,694,881 A | 9/1987 | Busk | |
| 4,694,882 A | 9/1987 | Busk | |
| 5,040,589 A | 8/1991 | Bradley et al. | |
| 5,056,902 A | 10/1991 | Chinnock et al. | |
| 5,056,938 A | 10/1991 | Ahlman et al. | |
| 5,064,463 A | 11/1991 | Ciomek | |
| 5,280,389 A * | 1/1994 | Kunikane et al. | ............. 359/664 |
| 5,359,992 A | 11/1994 | Hori et al. | |

(Continued)

FOREIGN PATENT DOCUMENTS

| | | |
|---|---|---|
| CN | 101804457 A | 8/2010 |
| EP | 0227201 A1 | 7/1987 |

(Continued)

OTHER PUBLICATIONS

Japanese Patent Office Notice of Reasons for Rejection Application No. 2012-140683 Issued: Sep. 17, 2013 5 pages.

(Continued)

*Primary Examiner* — George Wyszomierski
*Assistant Examiner* — Ngoclan T Mai
(74) *Attorney, Agent, or Firm* — St. Onge Steward Johnston & Reens LLC

(57) ABSTRACT

The invention provides an endoscope having a lens holder, wherein the lens holder comprises a body containing a sintered feedstock and machined surfaces. The invention also provides a method of manufacturing the endoscope which comprises the steps of molding a metal blank by a MIM process, wherein the metal blank is "near net shape" and has a sprue, a post, and optionally an outer shell, machining the inner surfaces and then the outer surfaces of the metal blank to form a lens holder, installing a lens in the lens holder, and assembling the lens holder having the lens into the endoscope.

9 Claims, 5 Drawing Sheets

(56) References Cited

U.S. PATENT DOCUMENTS

| | | |
|---|---|---|
| 5,577,546 A | 11/1996 | Kjar et al. |
| 5,706,143 A | 1/1998 | Hipp |
| 5,835,865 A | 11/1998 | Bertholdt et al. |
| 5,848,350 A | 12/1998 | Bulger |
| 5,978,161 A | 11/1999 | Lemke |
| 5,989,493 A | 11/1999 | La Salle et al. |
| 5,993,507 A | 11/1999 | Baum et al. |
| 6,024,457 A | 2/2000 | Kawai et al. |
| 6,298,901 B1 | 10/2001 | Sakamoto et al. |
| 6,350,328 B1 | 2/2002 | Hostetler |
| 6,470,956 B2 | 10/2002 | Sakamoto et al. |
| 6,478,842 B1 | 11/2002 | Gressel et al. |
| 6,508,980 B1 | 1/2003 | Sachs et al. |
| 6,514,269 B2 | 2/2003 | Yamamoto |
| 6,522,477 B2 | 2/2003 | Anhalt |
| 6,619,370 B2 | 9/2003 | Sakamoto et al. |
| 6,633,438 B2 | 10/2003 | Anhalt |
| 6,669,898 B2 | 12/2003 | Gressel et al. |
| 6,790,252 B2 | 9/2004 | Smith et al. |
| 6,838,046 B2 | 1/2005 | Lu et al. |
| 6,860,316 B2 | 3/2005 | Wu et al. |
| 6,890,368 B2 | 5/2005 | Braillard et al. |
| 7,686,449 B2 | 3/2010 | Jannard et al. |
| 7,706,065 B2 | 4/2010 | Regan et al. |
| 7,762,960 B2 | 7/2010 | Timberlake et al. |
| 7,952,820 B2 * | 5/2011 | Taki et al. ............. 359/811 |
| 7,976,462 B2 * | 7/2011 | Wright et al. ............. 600/171 |
| 8,216,127 B2 * | 7/2012 | Zifeng et al. ............. 600/112 |
| 2002/0149858 A1 | 10/2002 | Anhalt |
| 2006/0242813 A1 | 11/2006 | Molz et al. |
| 2010/0022831 A1 * | 1/2010 | Zifeng et al. ............. 600/112 |

FOREIGN PATENT DOCUMENTS

| | | |
|---|---|---|
| EP | 1250881 A2 | 10/2002 |
| JP | S62169632 A | 7/1987 |
| JP | H0650329 A | 2/1994 |
| JP | H112751 A | 1/1999 |
| JP | H1189850 A | 4/1999 |
| JP | H11258479 A | 9/1999 |
| JP | 2000352656 A | 12/2000 |
| JP | 2002372660 A | 12/2002 |
| JP | 2004042127 A | 2/2004 |
| JP | 2004091823 A | 3/2004 |
| JP | 2006171346 A | 6/2006 |
| JP | 2009294540 A | 12/2009 |

OTHER PUBLICATIONS

European Search Report Application No. EP 12 17 5584 Completed: Oct. 14, 2013; Mailing Date: Oct. 21, 2013 5 pages.
Notice of Reasons for Rejection Application No. 2012-140683 Issued: Aug. 4, 2014 pp. 9.

* cited by examiner ically related to a method of manufacturing endoscopic camera components and, more particularly, to a method of manufacturing lens holders for use in endoscopic cameras.

ENDOSCOPIC CAMERA COMPONENT MANUFACTURING METHOD

FIELD OF THE INVENTION

The present invention is generally related to a method of manufacturing endoscopic camera components and, more particularly, to a method of manufacturing lens holders for use in endoscopic cameras.

BACKGROUND OF THE INVENTION

Endoscopes and endoscopic video cameras are now widely used by physicians during surgery to view inside body cavities. In an endoscopic surgical procedure, small incisions, called portals, are made in a patient. An endoscope or endoscopic video camera is inserted in one of the portals. Surgical instruments used to perform specific surgical tasks are inserted into other portals. The surgeon views the surgical site through the endoscope or endoscopic video camera to determine how to manipulate the surgical instruments in order to accomplish the surgical procedure. An advantage of performing endoscopic surgery is that, since the portions of the body that are cut open are minimized, the portions of the body that need to heal after surgery are likewise reduced. Moreover, during an endoscopic surgical procedure, only relatively small portions of the patient's internal organs and tissues are exposed to the open environment. This minimal opening of the patient's body lessens the extent to which a patient's organs and tissues are open to infection.

Typically, an endoscopic video camera contains an optical focusing lens and a focusing device that can be adjusted to optimize images transmitted by the endoscopic video camera. The focusing device usually utilizes magnetic drives to move or rotate the focusing lens axially within the lens holder. As such, the lens holder is a small yet convoluted part of the endoscopic video camera. For example, the endoscopic video cameras described in U.S. Pat. No. 5,359,992 issued to Hori et al., and U.S. Pat. No. 5,056,902 issued to Chinnock et al. require the lens holders adapted to the mechanical linkages between the internal magnets and the lens, and the movement of the lens within the interior chamber in response to the rotation of external magnets located around the periphery of the interior chamber; and the endoscopic video cameras described in U.S. Pat. No. 5,978,161 issued to Lemke, U.S. Pat. No. 5,835,865 issued to Speier et al., and U.S. Pat. No. 5,706,143 issued to Hipp require lens holders having helical grooves, magnet seats and mechanical linkages to connect the internal magnets to the lens, or require the internal magnet to travel within a helical channel in order to convert the rotational movement of the internal magnets to linear movement of the lens.

In an effort to simplify the magnetic focusing device and to solve various shortcomings associated with the complicated endoscopic video cameras, U.S. Pat. Nos. 6,522,477 and 6,633,438, both issued to Anhalt, disclose endoscopic video cameras which do not require a mechanical linkage between the lens and internal magnets. The lens holders in Anhalt have the following structures, as illustrated in FIG. 1. A zoom lens holder 10a can be in the form of a raceway around the periphery of the lens (not shown) with a set of symmetrical protrusions or legs which are evenly spaced and extend proximally from the raceway in one direction which define the path of the lens during operation. A fixed lens holder 10b can be in the form of a raceway around the periphery of the lens with two sets of symmetrical protrusions or legs, with the first set of protrusions or legs extending proximally from the raceway in one direction, and the second set of protrusions or legs extending distally from the raceway in the opposite direction. Anhalt also discloses a simple lens holder 10c that does not contain any protrusions or legs extending from the raceway.

Because the lens holders play an important role in the performance of the endoscopic video cameras, it is critical that the lens holders be manufactured with precision.

Traditionally, the lens holders are manufactured from solid metal bar stocks by 100% machining, as illustrated in FIG. 2. This manufacturing method unavoidably results in high manufacturing cost in terms of material used (and wasted) and the machining time. Using this manufacturing method, it is difficult, if not impossible, to machine the lens holders with consistent precision. Therefore, the traditional 100% machining is not suitable for a high volume production of the lens holders.

In recent years, metal injection molding ("MIM") processes have been used to manufacture various components in medical or optical instruments, as disclosed in U.S. Pat. Nos. 7,762,960, 6,514,269, 7,706,065 and 7,686,449; and U.S. Pat. Appln. No. 20060242813. The teachings of these patents are incorporated herein by references in its entirety.

In a typical MIM process, a metal powder is mixed with a binder to form a homogenous liquid mixture. The mixture is injected into a die or mold which is then subjected to high pressure to form a "green" metal blank, which typically is about 60% dense. The binder in the "green" metal blank is then burned off or removed chemically and the resulting skeleton, called "brown" metal blank, is sintered to near full density. Compared to the traditional 100% machining and other deposition techniques such as casting, stamping, and lithography, the MIM process greatly saves the material used for manufacturing and allows a high volume production with reasonable consistency in quality. The MIM process is also versatile at producing small components having complex internal and external shapes.

One long and continuing problem encountered with the MIM process is the shrinkage of metal blanks from the "green" stage. The shrinkage problem is generally more obvious in complex metal blanks, due to uneven shrinkages of the interior and exterior configurations after sintering. Another problem of the MIM process is that sintered metal blanks usually require a great extent of metal conditioning treatment in order to arrive at the desired dimensions of the final components. The metal conditioning treatment to sintered metal blanks is often referred as "secondary machining" or "post machining." As with all machining, more secondary machining means more machining time and higher manufacturing cost.

To overcome the shrinkage problem encountered by typical the MIM process, U.S. Pat. No. 6,508,980 to Sachs, et al. ("Sachs") provides a two-material sintering method. In contrast to a conventional method where a binder is removed and the powder particles themselves sintered together to provide a shrunken final component, in Sachs the material that joins the powder particles is provided as an independent material and there is no movement of the powder particles after they have been placed during sintering. Although the skeleton shrinkage may be avoided, the method in Sachs requires two different metal materials and the repeated steps of adding the second independent material into the matrix of the first material and binding the first and second materials.

What is desired, therefore, is an improved manufacturing method for an endoscopic camera component, such as a lens holder for an endoscope, which efficiently utilizes metal materials, minimizes secondary machining, shortens the overall manufacturing time, and increases consistency in the component quality. It is also desirable that such manufacturing method is sufficiently versatile to be applied to various types of lens holders and other similar types of metal components.

SUMMARY OF THE INVENTION

The present invention provides a method of manufacturing an endoscope having at least one lens holder. The method comprises the steps of molding at least one brown metal blank by a metal injection molding (MIM) process, wherein the at least one brown metal blank has a sprue and a post, and is substantially similar in size and shape to the at least one lens holder, machining the at least one brown metal blank to form the at least one lens holder, installing a lens in each of the at least one lens holder, and assembling the at least one lens holder having the lens into an endoscopic tube to form an endoscope. One aspect of the invention is that minimal machining is required to form the at least one lens holder because the at least one brown metal blank is substantially similar in size and shape to the at least one lens holder. By using the MIM process, the present invention also achieves higher material utilization and increased quality control of the finished components, e.g. the lens holders.

In a preferred embodiment, the step of machining comprises the steps of machining the inside dimensions of the at least one brown metal blank, and then machining the outside dimensions of the at least one brown metal blank using the inside machined surfaces as a reference to form the at least one lens holder. By using the inside surfaces as a reference, the final outside surfaces can be precisely grinded to the final dimensions with tight tolerances. This is another aspect of the present invention.

In a less preferred embodiment, the machining step may start with machining the outer surfaces of the brown metal blank, followed by machining the inside surfaces.

In one embodiment, the sprue and the post of the at least one brown metal blank are trimmed for ease of handling before machining the at least one brown metal blank. This is a further aspect of the present invention.

In another embodiment, the at least one brown metal blank contains an outer shell which supports and strengthens the at least one brown metal blank from damage during the molding and machining steps. In this embodiment, machining the inside surfaces can be performed by holding the at least one brown metal blank from the outer shell. The outer shell also prevents deflecting the extrusions of the component during machining. This is yet another aspect of the present invention.

In another embodiment, lubricants are applied to the at least one lens holder using DICRONITE® (i.e., tungsten disulfide ($WS_2$)) coating process before a lens is installed in the at least one lens holder.

The present invention also provides an endoscope having at least one lens holder which comprises a body containing a sintered feedstock, a machined inside surface, and a machined outside surface.

In one embodiment, the body of the at least one lens holder has a raceway and a set of extrusions extending from the periphery of said raceway in one direction.

In another embodiment, the body of the at least one lens holder has a raceway, a first set of extrusions extending from the periphery of said raceway in one direction, and a second set of extrusions extending from the periphery of said raceway in an opposite direction.

DETAILED DESCRIPTION OF THE INVENTION

The present invention provides a method of manufacturing an endoscope having one or more lens holders. The terms "endoscope" and "endoscopic video camera" are used interchangeably in this Application.

Figure 1:
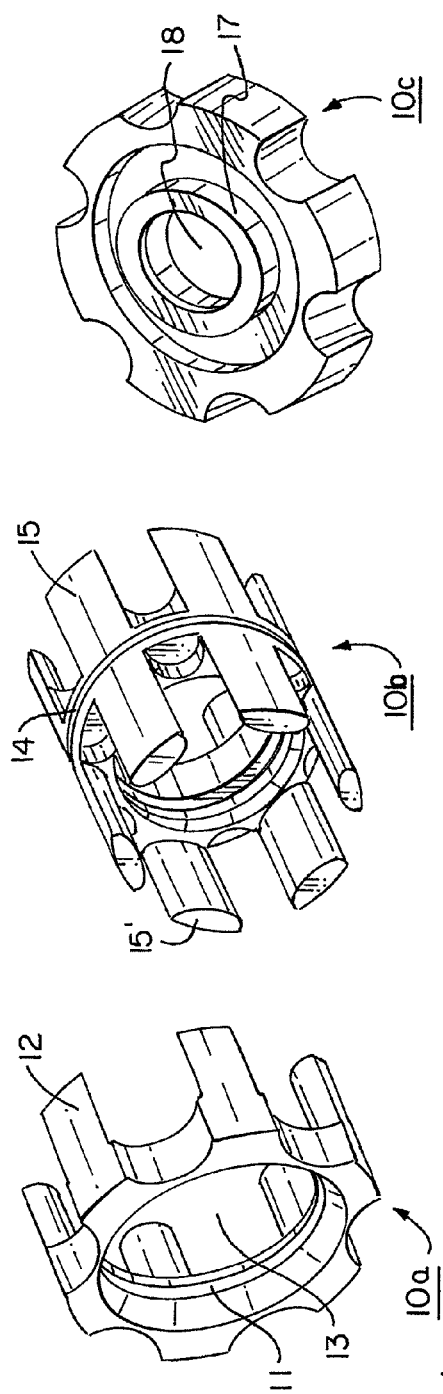
FIG. 1 illustrates various types of lens holders as disclosed in U.S. Pat. Nos. 6,522,477 and 6,633,438, to Anhalt, a prior art.
Figure 2:
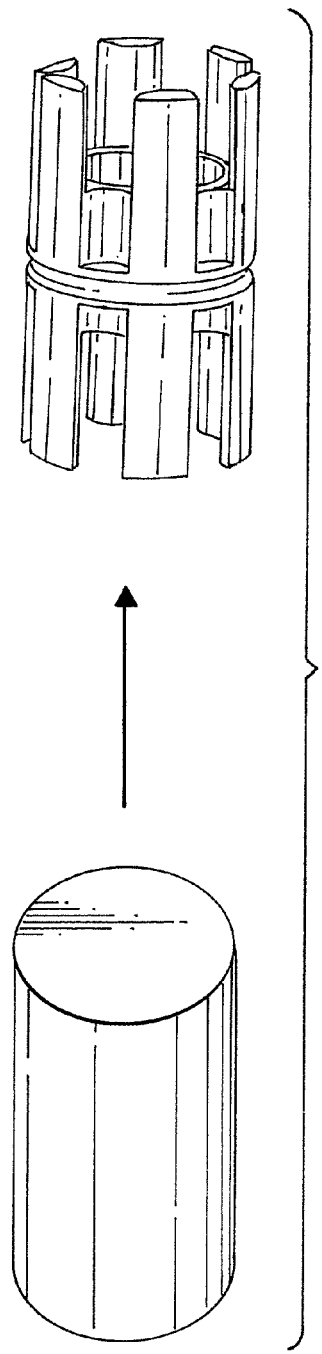
FIG. 2 illustrates the 100% machining method for manufacturing lens holders in accordance with another prior art.
Figure 3:
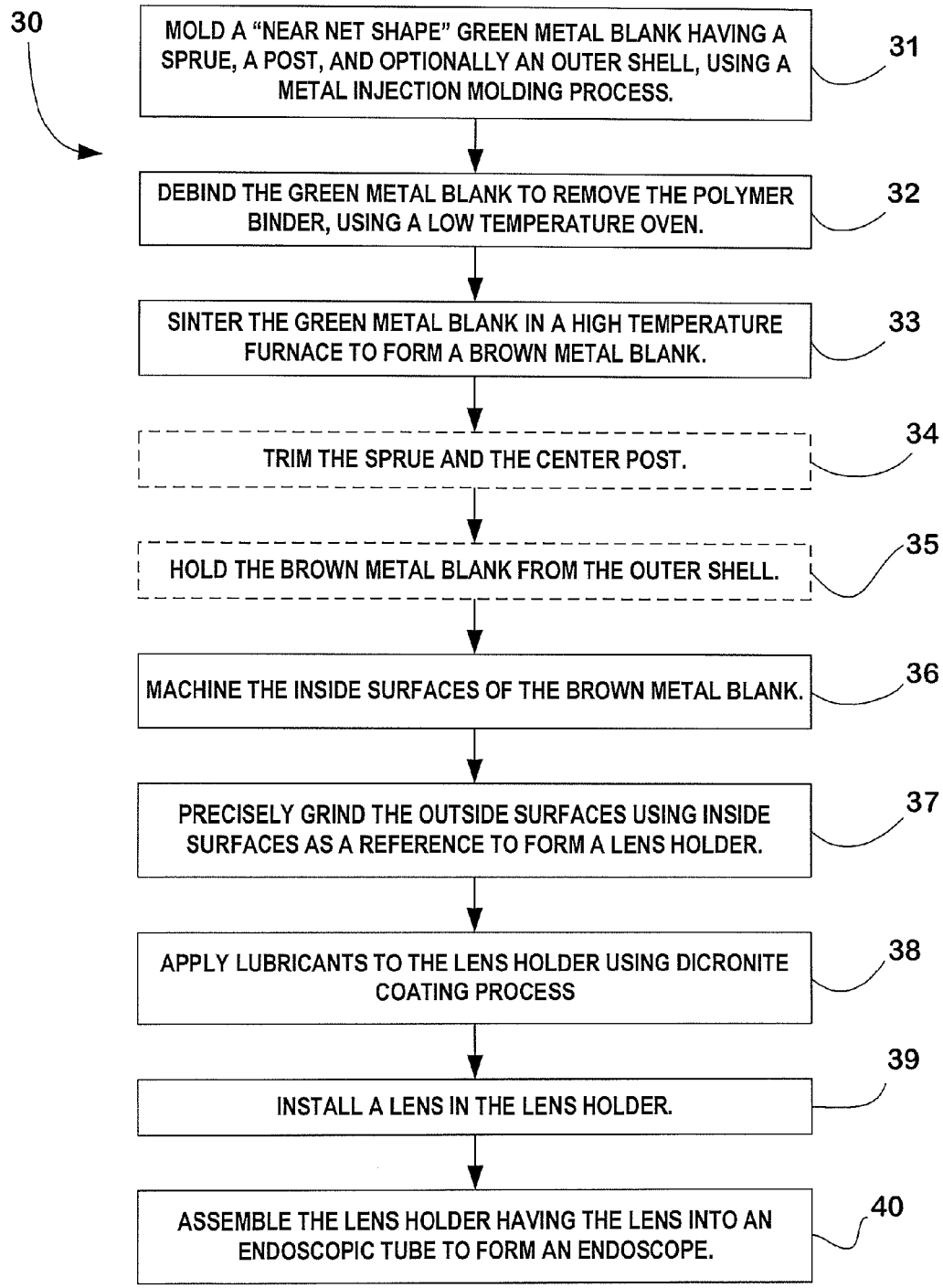
FIG. 3 illustrates various steps of the manufacturing method in accordance with one embodiment.

FIG. 3 illustrates various steps of the manufacturing method 30 in accordance with the present invention. The first few of steps, 31 to 37, are devoted to the steps of manufacturing the lens holders which utilizes a near net machining concept. Under this concept, a metal blank, also called MIM blank, which includes all molding features, e.g. gating, sprue, ejection pin marks, parting line, post, is first molded by a metal injection molding (MIM) process to a "near net shape" of the final component such that minimal secondary machining is required to complete the final component.

The term "MIM process" refers to the process which combines metal powders with binder materials to produce a 'feedstock' that is injected as a liquid into a hollow mold using plastic injection molding machines, followed by the binder removal and the sintering step to solidify the molded metal component. The MIM process is a superior process as compared to forging, casting, or other processes in that it allows an arbitrary selection of the shape of the metal body, including irregular shapes, and in that it is suitable for mass production at a lower cost, and in that the sintered product has excellent physical and mechanical properties as a result of the improved compaction obtained by use of fine powder. In addition, the MIM process can achieve tighter tolerance than other processes, e.g. casting, extrusion, or forging. The MIM process and the feedstock for use therein have been described, for example, in U.S. Pat. Nos. 4,694,881, 4,694,882, 5,040,589, 5,064,463, 5,577,546, 5,848,350, 6,860,316, 6,890,368, 6,838,046, 6,790,252, 6,669,898, 6,619,370, 6,478,842, 6,470,956, 6,350,328, 6,298,901, 5,993,507, 5,989,493, and U.S. Pat. Appln. No. 20060242813, the disclosures of each of which are incorporated herein in their entirety.

The properties of the metal powders determine the final properties of the MIM product. Any metal or metal alloys capable of implementation within the MIM feedstock and responding to the magnet field created by external magnets can be used for fabricating the MIM blank for this invention. Suitable metal or metal alloys for the present invention include, but not limiting to, stainless steel, aluminum, nickel, brass, titanium, tantalum, iron, phosphor bronze, tungsten, gold, silver, copper, cobalt, chromium or alloys thereof. The preferred metal for the lens holders is magnetic stainless steel.

The term "near net shape" means that the metal blank is substantially similar to the final component in terms of shapes and dimensions.

The first step 31 is molding a "near net shape" green metal blank having a sprue, a post, and optionally an outer shell, using a metal injection molding process.

The second step 32 is debinding the green metal blank to remove the polymer binder using a low temperature oven followed by step 33, sintering the green metal blank in high temperature furnace to fuse the metal powder together to form "near net shape" brown metal blank.

Figure 4:
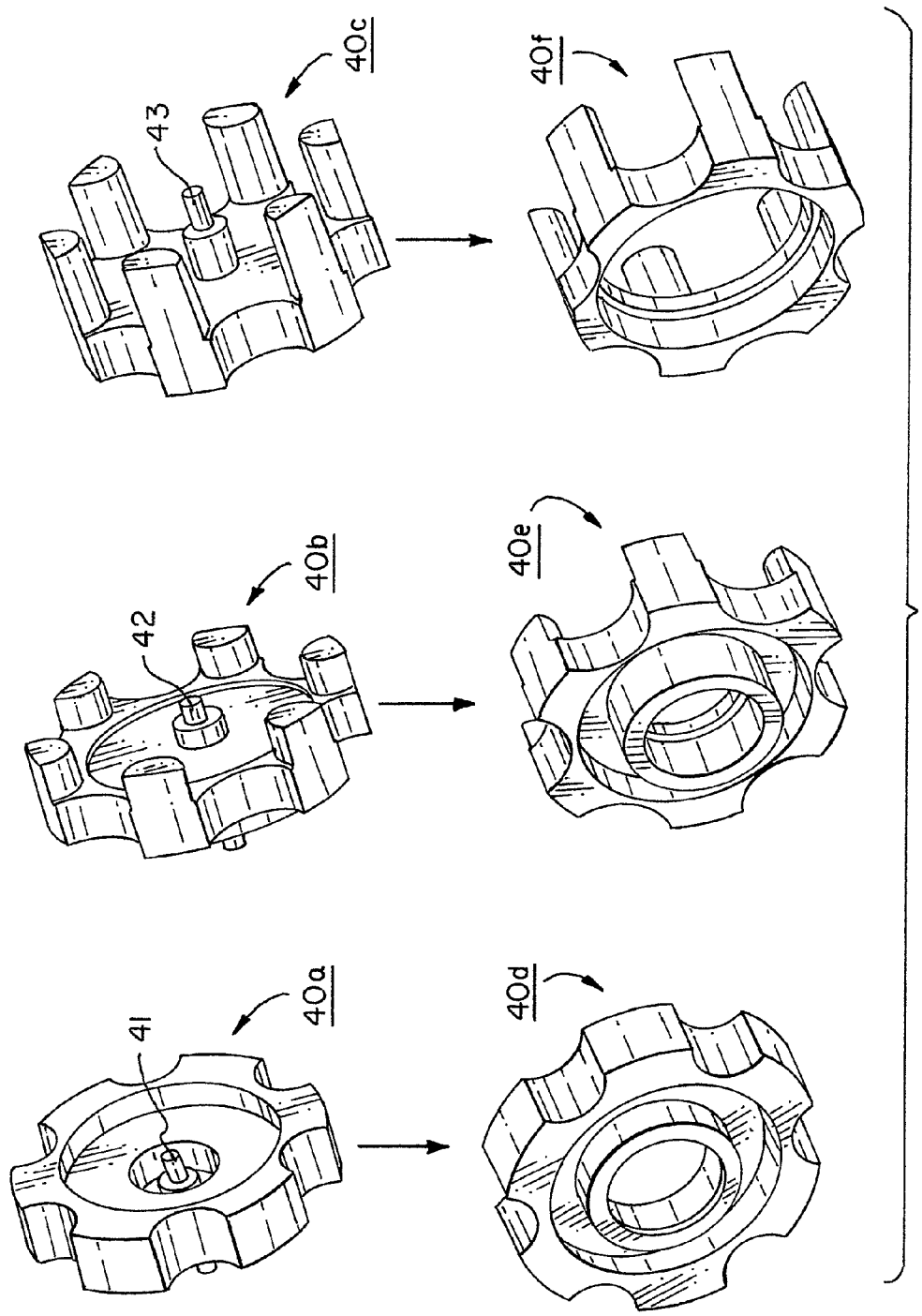
FIG. 4 illustrates a number of zoom lens holders during various steps of the manufacturing method.
Figure 5:
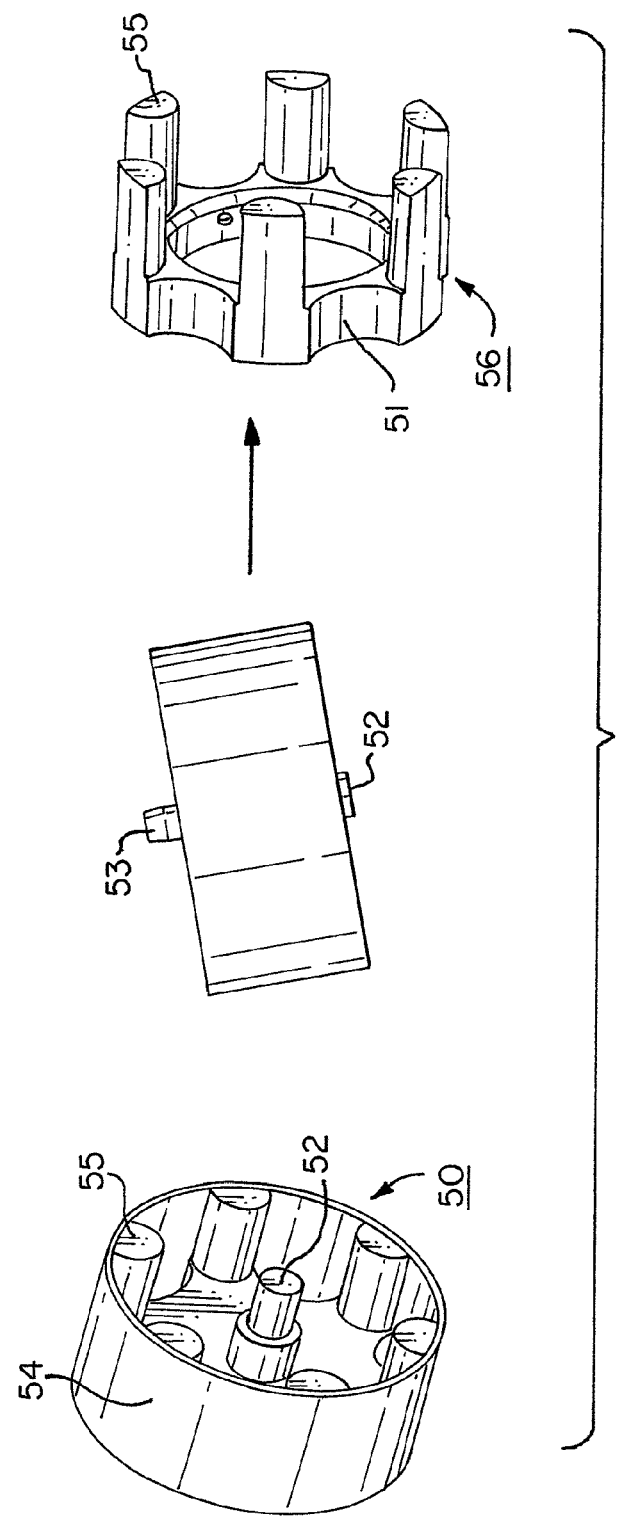
FIG. 5 illustrates a zoom lens holder during various steps of the manufacturing method.
Figure 6:
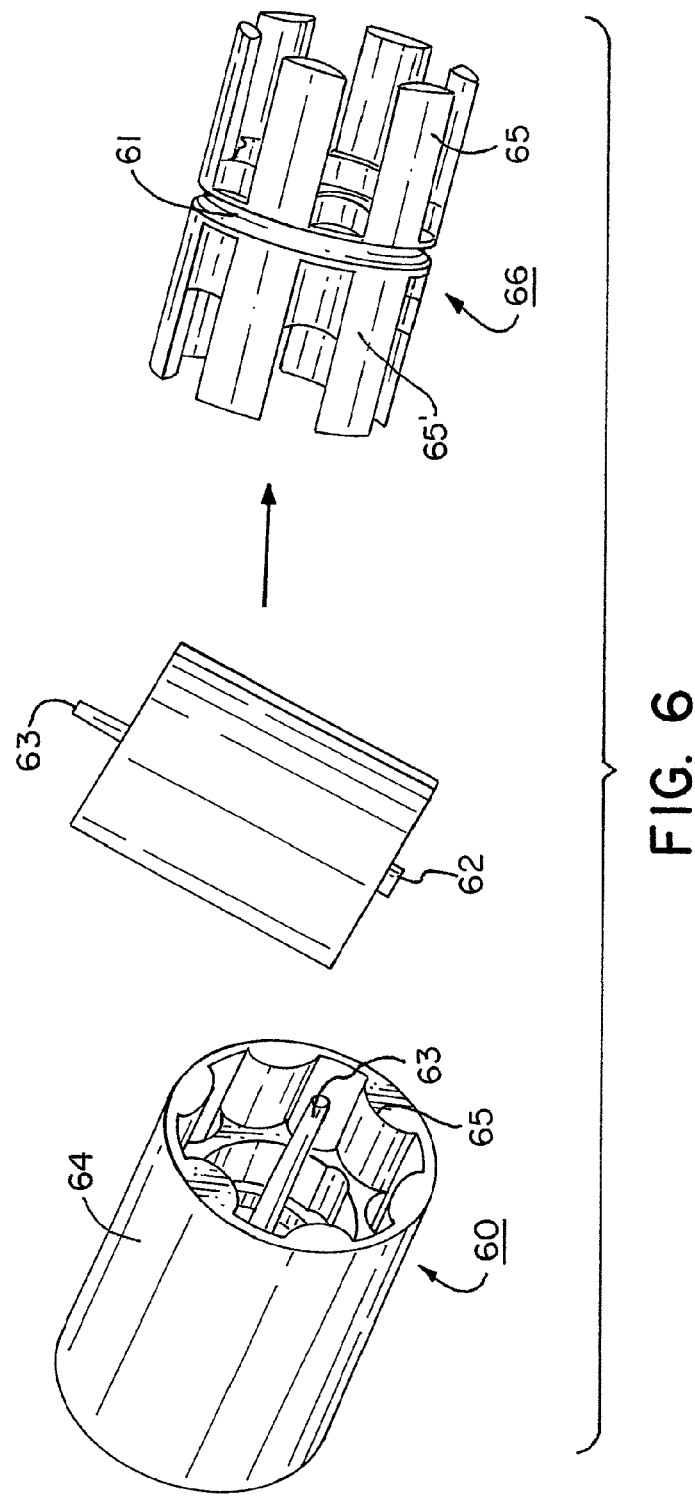
FIG. 6 illustrates a fixed lens holder during various steps of the manufacturing method.

FIGS. 4 to 6 illustrate different types of "near net shape" brown metal blanks having a sprue and a post during a manufacturing method in accordance with the present invention.

FIG. 4 shows that a metal blank 40a,40b,40c which has an inner surface and an outer surface. The metal blank 40a,40b, 40c has a center post 41,42,43 which is positioned in the center of the blank 40a,40b,40c and which forms an integrated part of the metal blank 40a,40b,40c. The metal blank 40a,40b,40c has a spruce (not shown) at the opposite end of the post 41,42,43.

FIGS. 5 and 6 show that a metal blank 50,60 which has an inner surface and an outer surface. The metal blank 50,60 has a center post 52,62 and a spruce 53,63 which locates at the opposite end of the center post 52,62. Both the center post 52,62 and a spruce 53,63 form an integrated part of the metal blank 50,60.

The center post 41,42,43,52,62 provides support to the center material of the metal blank 40a,40b,40c,50,60 and prevents it from slumping during the sintering step. The center post 41,42,43,52,62 and sprue 53,63 provides an additional means for handling the metal blank 40a,40b,40c,50,60 during the manufacturing process. For instance, they are able to set the blank 40a,40b,40c,50,60 in the sintering fixture without having the blank surface in touch of the fixture surface to avoid the constraints of shrinkage at the blank surface during sintering because of the friction between the blank surface and the fixture surface. Preferably, the center post 41,42,43,52,62 extends beyond the bottom surface of the metal blank 40a,40b,40c,50,60 to provide sufficient clearance between the bottom surface of the metal blank and the surface of the sintering fixture.

The metal blank 50,60 may optionally comprise an outer shell 54,64, which forms an integrated part of the metal blank 50,60. As illustrated in FIGS. 5 and 6, the outer shell 54,64 has an interior surface and an exterior surface. The interior surface of the outer shell 54,64 is in contact with the outer surface of the metal blank 50,60, and particularly, partial or all peripheries of the extrusions/legs 55,65,65' and the raceway 51,61 of the metal blank 50,60. Preferably, the outer shell 54,64 substantially covers the rest parts of metal blank 50,60. The outer shell 54,64 provides advantageous structure support to the metal blank 50,60 during the sintering and machining steps. It not only prevents the fragile extrusions/legs 55,65,65' from damage and strength the green state material of the metal blank 50,60, but also allows for a more uniform shrinkage during the sintering step. During the step of machining the inside surfaces, the outer shell prevents deflecting any extrusion of the component. The outer shell is beneficial when the lens holder has long extrusions/legs, e.g. the zoom lens holder in FIG. 5 and the fixed lens holder in FIG. 6. When the metal blank has no or relatively short extrusions/legs, the outer shell is not necessary, e.g. the various lens holders in FIG. 4.

The thickness of the outer shell 54,64 may vary, but necessarily depends on the type of metal used and the extent of secondary machining. The outer shell 54,64 should be sufficiently strong to stand the impacts from the secondary machining.

The next step 34 is optional for the manufacturing method in accordance with the present invention. In this step 34, the sprue 53,63 and the post 52,62 are trimmed for ease of handling.

If the metal blank 50,60 has the outer shell 54,64, the manufacturing method may optionally have the step 35 in which the metal blank 50,60 is held from the outer shell 54,64 for ease of handling, for example, during the step of machining the inside surface of the metal blank 50,60.

A person with ordinary skilled in the art would understand that steps 34 and 35 can be performed in reversed order.

During the next steps 36 and 37, the metal blank 40a,40b, 40c,50,60 is post machined to the required specifications of the lens holder 40d,40e,40f,56,66. The term "machining" or "machined" refers to the conventional metalworking processes such as heat treatments and/or surface treatments such as abrading, cutting, drilling, forming, grinding, and/or shaping of a piece of metal into the desired final piece using by machine tools such as lathes, power saws, and presses. The center post, and the outer shell if any, may be removed during the secondary machining or at the end of the machining, depending on the geometry of the component and the need to access to certain parts of the component. Because the metal blank 40a,40b,40c,50,60 is "near net shape" of the lens holder 40d,40e,40f,56,66, minimal machining is required to form the desired lens holder. Less machining means less machining time and lower manufacturing cost.

Comparing to the prior art in which the lens holder is manufactured by 100% machining from a solid bar stock, the present method avoids material waste, saves machining time, and improves the quality consistency of the finished lens holders.

The machining steps 36,37 are typically performed by the step of machining the inside dimensions of the metal blank 36, followed by the step of machining the outside dimensions of the metal blank using the inside machined surfaces of the metal blank 37. By using the inside surfaces as a reference, the final outside surface can be precisely grinded to the final dimensions with tight tolerances which cannot be achieved by a direct molding process. Conventional Computer Numerical Controlled (CNC) milling is unable to accomplish the outside diameter as the interrupt cutting action will deflect any extrusions of the metal blank during the operation and affect the final dimensions.

A person skilled in the art would understand that the machining steps can be performed in a less preferred order, for instance, by the step of machining the outer surfaces of the metal blank first 37, followed by the step of machining the inner surfaces 36, and optionally using the outer surfaces as a reference, to form the lens holder.

Optionally, lubricants are applied to the lens holder using DICRONITE® (i.e., tungsten disulfide ($WS_2$)) coating process, step 38. After that, a lens is installed in the lens holder, the step 39. Then the lens holder installed with the lens is assembled into an endoscopic tube to form an endoscope, the step 40.

A person with ordinary skill in the art would understand that, in the event that an endoscope contains more than one lens holder, each lens holder can be manufactured in accordance with same or different embodiments of the present invention. Additionally, more than one lens may be installed in a lens holder and different type of lenses can be installed in the same or different lens holders.

The present invention also provides an endoscope having one or more lens holders, wherein the lens holder comprises a body which in turn comprises a sintered feedstock, a machined inside surface, and a machined outside surface. The feedstock is preferably made by stainless steel.

The lens holders of the present invention distinguish from the prior art lens holders in that the body of the lens holders of the present invention contains a sintered feedstock, whereas the body of the prior art lens holders is made up by 100% metal stock. Because the sintered feedstock has gone through a high temperature treatment during the sintering step in the MIM process, the properties of two bodies are different from each other. For instance, the sintered feedstock usually has a higher density and durability than that of the metal stock.

The body of the lens holders may have various shapes and dimensions as illustrated in FIGS. 4 to 6. In one embodiment, a lens holder 40e,40f,56 has a raceway 45,46,51 with a set of symmetrical extrusions/legs 47,48,55 which are evenly spaced and extend from the raceway 45,46,51 in one direction. In another embodiment, a lens holder 66 has a raceway 61 with two sets of symmetrical extrusions/legs 65,65' with the first set of extrusions/legs 65 extending proximally from raceway 61 in one direction, and the second set of extrusions/legs 65' extending distally from raceway 61 in the opposite direction. In yet another embodiment, a simple lens holder 40d has no protrusions extending from the raceway 44. All these lens holders share two common structure features. First, their exterior shape, defined by the periphery of the raceway 44,45,46,51,61 and/or the extrusions/legs 447,48,55,65,65' is generally of cylinder shape, such that an outer shell of sleeve shape is able to cover the lens holders during the manufacturing steps. Second, they have a lengthwise hollow center for holding a lens.

The foregoing detailed description is provided to describe the invention in detail, and is not intended to limit the invention. Those skilled in the art will appreciate that various modifications may be made to the invention without departing significantly from the spirit and scope thereof.

What is claimed is:

1. A method of manufacturing an endoscope having at least one lens holder comprising the steps of:
    forming at least one green metal blank using metal injection molding of a feedstock having metal powders and polymer binders, said at least one green metal blank comprising a sprue, a post and an outer shell, said at least one green metal blank having inside dimensions and outer dimensions, and said at least one green metal blank substantially similar in size and shape to said at least one lens holder;
    debinding said at least green metal blank to remove said polymer binders using a low temperature oven to form at least one debinded green metal blank;
    sintering said at least one debinded green metal blank in a high temperature furnace to form at least one brown metal blank;
    holding said at least one brown metal blank from said outer shell and
    machining said at least one brown metal blank to form said at least one lens holder, wherein said sprue, said post and said outer shell are removed during or at the end of the machining;
    installing a lens in each of said at least one lens holder; and
    assembling said at least one lens holder installed with said lens into said endoscope.

2. The method of manufacturing an endoscope having at least one lens holder according to claim 1, wherein the step of machining said at least one brown metal blank to form said at least one lens holder comprises the steps of:
    machining said inside dimensions of said at least one brown metal blank; and
    machining said outside dimensions of said at least one brown metal blank using said inside dimensions of said at least one brown metal blank as a reference to form said at least one lens holder.

3. The method of manufacturing an endoscope having at least one lens holder according to claim 1, further comprising before said step of machining said at least one brown metal blank, the step of trimming said sprue and said post of said at least one brown metal blank.

4. The method of manufacturing an endoscope having at least one lens holder according to claim 3, wherein said step of machining said at least one brown metal blank to form said at least one lens holder comprises the steps of:
    machining said inside dimensions of said at least one brown metal blank; and
    machining said outside dimensions of said at least one brown metal blank using said inside dimensions of said at least one brown metal blank as a reference to form said at least one lens holder.

5. A method of manufacturing an endoscope having at least one lens holder comprising the steps of:
    forming at least one green metal blank using metal injection molding of a feedstock having metal powders and polymer binders, said at least one green metal blank comprising a sprue, a post and an outer shell, said at least one green metal blank having inside dimensions and outer dimensions, and said at least one green metal blank substantially similar in size and shape to said at least one lens holder;
    debinding said at least green metal blank to remove said polymer binders using a low temperature oven to form at least one debinded green metal blank;
    sintering said at least one debinded green metal blank in a high temperature furnace to form at least one brown metal blank;
    machining said at least one brown metal blank to form said at least one lens holder;
    applying a tungsten disulfide lubricative coating to said lens holder;
    installing a lens in each of said at least one lens holder; and
    assembling said at least one lens holder installed with said lens into said endoscope.

6. The method of manufacturing an endoscope having at least one lens holder according to claim 1, wherein said step of machining said at least one brown metal blank to form said at least one lens holder comprises the steps of:
    machining said outside dimensions of said at least one brown metal blank; and
    machining said inside dimensions said at least one brown metal blank using said outside dimensions of said at least one brown metal blank as a reference to form said at least one lens holder.

7. The method of manufacturing an endoscope having at least one lens holder according to claim 1, wherein said at least one brown metal blank is made of stainless steel.

8. A method of manufacturing an endoscope having at least one lens holder comprising the steps of,
    forming at least one green metal blank using metal injection molding of a feedstock having metal powders and polymer binders, said at least one green metal blank comprising a sprue, a post and an outer shell, said at least one green metal blank having inside dimensions and outer dimensions, and said at least one green metal blank substantially similar in size and shape to said at least one lens holder;
    debinding said at least green metal blank to remove said polymer binders using a low temperature oven to form at least one debinded green metal blank;
    sintering said at least one debinded green metal blank in a high temperature furnace to form at least one brown metal blank;
    machining said at least one brown metal blank to form said at least one lens holder;

installing a lens in each of said at least one lens holder; and
assembling said at least one lens holder installed with said lens into said endoscope;
wherein said at least one lens holder has a raceway and a set of extrusions extending from the periphery of said raceway in one direction.

9. The method of manufacturing an endoscope having at least one lens holder according to claim 8, wherein said at least one lens holder has a second set of extrusions extending from the periphery of said raceway in a direction opposite to said one direction.

* * * * *